US008721983B2

(12) United States Patent
Yokoi et al.

(10) Patent No.: US 8,721,983 B2
(45) Date of Patent: May 13, 2014

(54) STERILIZER

(75) Inventors: Yasuhiko Yokoi, Gunma (JP); Hiroshi Yamamoto, Osaka (JP); Atsushi Nakao, Osaka (JP); Jiro Ohnishi, Gunma (JP); Shinji Fukui, Gunma (JP); Akifumi Iwama, Ibaraki (JP); Masaki Harada, Kyoto (JP); Yoshiaki Sugimura, Osaka (JP); Katsuya Hirai, Osaka (JP)

(73) Assignee: Panasonic Healthcare Co., Ltd., Ehime (JP)

( * ) Notice: Subject to any disclaimer, the term of this patent is extended or adjusted under 35 U.S.C. 154(b) by 909 days.

(21) Appl. No.: 12/748,663

(22) Filed: Mar. 29, 2010

(65) Prior Publication Data
US 2011/0027146 A1 Feb. 3, 2011

(30) Foreign Application Priority Data
Jul. 30, 2009 (JP) .............................. P2009-178086

(51) Int. Cl.
A61L 2/20 (2006.01)
(52) U.S. Cl.
USPC .......................................... 422/292; 422/211
(58) Field of Classification Search
USPC ................................................. 422/292, 211
See application file for complete search history.

(56) References Cited

U.S. PATENT DOCUMENTS

| 5,792,435 | A | 8/1998 | Mueller et al. |
| 5,861,305 | A | 1/1999 | Silley et al. |
| 2007/0212282 | A1 | 9/2007 | Matsui et al. |
| 2008/0080999 | A1* | 4/2008 | Bondar ........................... 422/31 |
| 2008/0213873 | A1 | 9/2008 | Murray et al. |

FOREIGN PATENT DOCUMENTS

| GB | 2 393 393 A | 3/2004 |
| JP | 10-507075 A | 7/1998 |
| JP | 11319046 A | 11/1999 |
| JP | 2001-340432 A | 12/2001 |
| JP | 2002-301138 | 10/2002 |
| JP | 3104211 U | 9/2004 |
| JP | 2005-278565 A | 10/2005 |
| JP | 2006-068122 | 3/2006 |
| JP | 2007-508025 A | 4/2007 |
| JP | 2007-195956 A | 8/2007 |
| JP | 2007195772 A | 8/2007 |
| JP | 2010-051351 A | 3/2010 |

OTHER PUBLICATIONS

English language machine translation of JP 2006 068122 A, publsihed Mar. 16, 2006.*
European Search Report issued in European Patent Application No. 10003303.4-2113, mailed Jun. 18, 2010.

* cited by examiner

Primary Examiner — Sean E Conley
(74) Attorney, Agent, or Firm — McDermott Will & Emery LLP

(57) ABSTRACT

A sterilizer is connectable to an external chamber. A sterilization gas generator is configured to generate sterilization gas. A gas supply system including a first gas supply system which is configured to supply the sterilization gas from the sterilization gas generator to a sterilization chamber; and a second gas supply system which is different from the first gas supply system and configured to supply the sterilization gas from the sterilization gas generator to the external chamber.

18 Claims, 13 Drawing Sheets

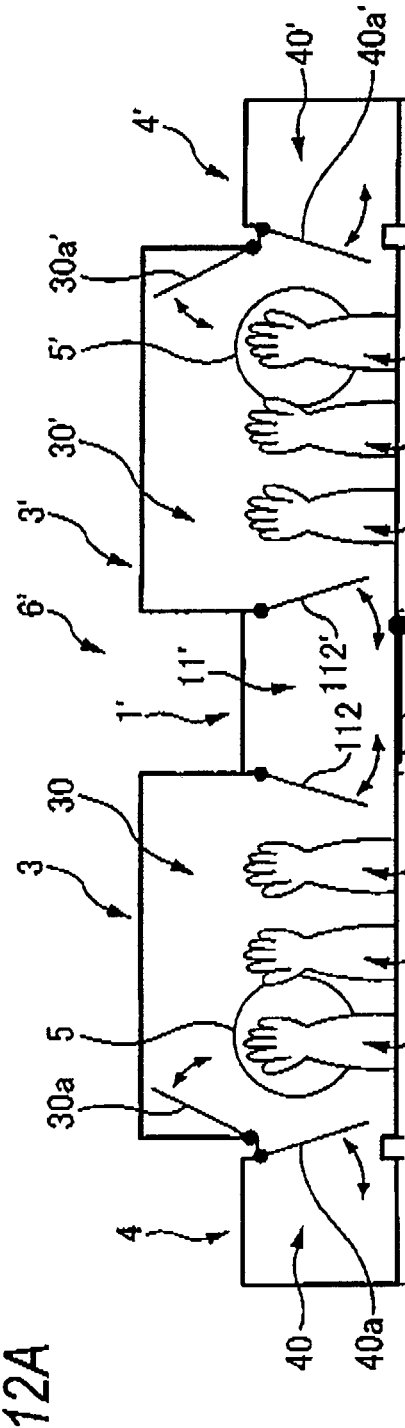
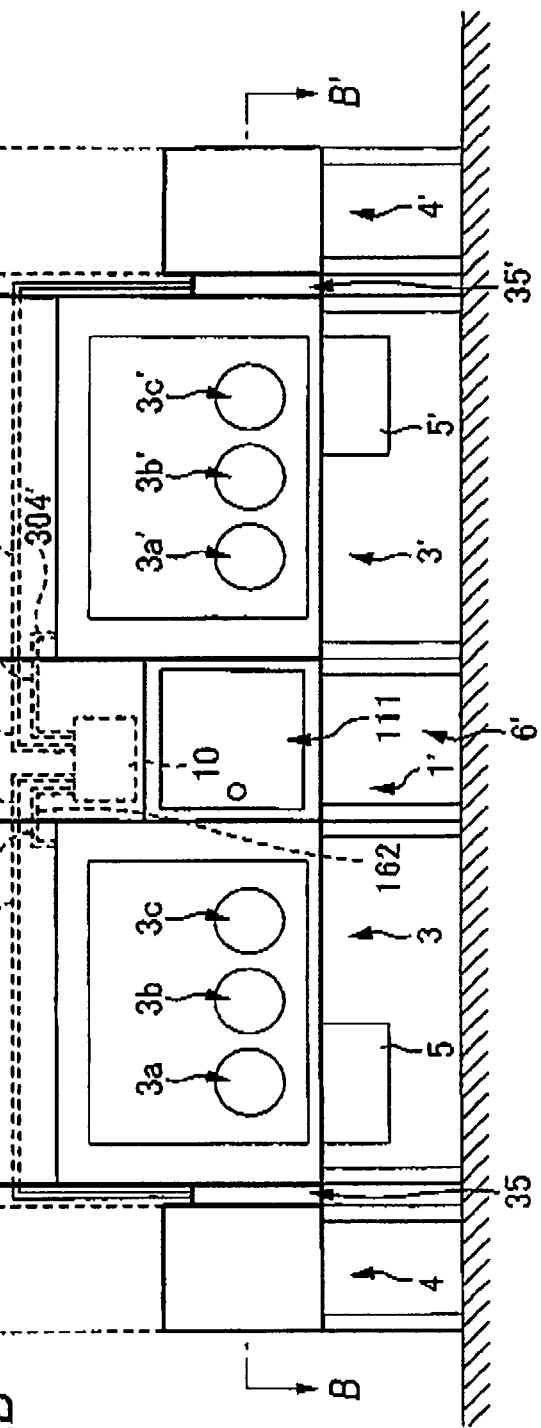
FIG. 12A
FIG. 12B

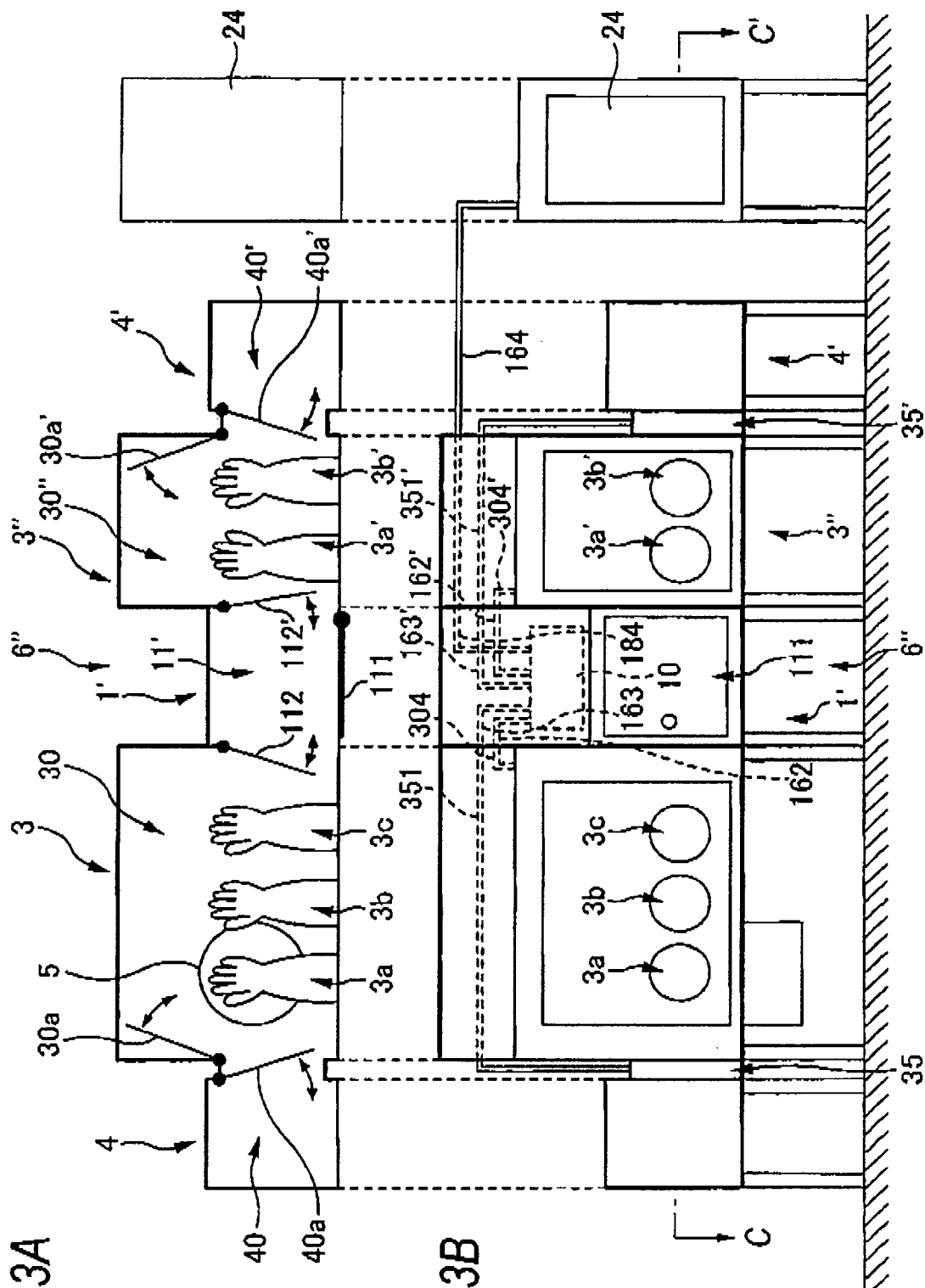

STERILIZER

The disclosure of Japanese Patent Application No. 2009-178086 filed on Jul. 30, 2009 including specification, drawings and claims is incorporated herein by reference in its entirety.

BACKGROUND

The present invention relates to a sterilizer.

An isolator isolated from external air is connected to an incubator so as to perform a predetermined pretreatment on cells to be cultured by the incubator in a sterilized manner. A sterilization box isolated from external air is connected to this isolator so as to sterilize the cells or articles necessary for cultivation before the cells or articles are brought in the isolator (for example, see Japanese Patent Publication No. 2002-301138A).

This sterilization box includes sterilizing means such as a sterilization gas generator. For example, an operator first brings the cells or the articles in a chamber of the sterilization box in a state where a door which isolates a chamber of the isolator from the chamber of the sterilization box is closed, and sterilizes the cells or the articles in the chamber of the sterilization box. Next, the operator opens the door and brings in the cells or the articles which have been sterilized in the chamber of the sterilization box, in the chamber of the isolator which is maintained in a sterile state.

The term "perform a predetermined pretreatment in a sterilized manner" means that the pretreatment is performed in a sterile environment. The term "sterile environment" refers to a nearly dust-free and bacteria-free environment for preventing mixture of materials other than materials necessary for the operation. The term "sterilization" indicates a processing for establishing the sterile environment.

The sterilization includes 1) a pretreatment process, 2) a gas exposure process, and 3) a substitution process. Specifically, 1) the pretreatment process is a preparation process including a leakage test of a sterilization target space and performed before sterilization gas is supplied, 2) the exposure process is a process for supplying the sterilization gas to the sterilization target space, and 3) the substitution process is a process in which the sterilization gas remained in the sterilization target space is detoxified, discharged, and substituted with external air.

For example, after the cells cultured by the incubator are brought out of the sterilization box through the isolator, the isolator may be sterilized again. In this case, in the isolator and the sterilization box described in Japanese Patent Publication No. 2002-301138A, sterilization gas is generated from a sterilization gas generator in a state where the door which isolates the chamber of the isolator and the chamber of the sterilization box and is introduced into the chamber of the isolator through the chamber of the sterilization box for sterilization of the chamber of the isolator. With this configuration, however, the sterilization efficiency is unsatisfactory, and thus it takes a lot of time to perform sterilization processing.

Meanwhile, if the sterilizing means is also provided in the isolator, the sterilization efficiency in the chamber is improved, but two the sterilizing means are provided separately in the isolator and the sterilizer, which leads to as much of an increase in equipment cost.

SUMMARY

According to an aspect of at least one embodiment of the present invention, there is provided a sterilizer which is connectable to an external chamber, the sterilizer comprising: a sterilization gas generator configured to generate sterilization gas; a sterilization chamber; and a gas supply system including: a first gas supply system which is configured to supply the sterilization gas from the sterilization gas generator to the sterilization chamber; and a second gas supply system which is different from the first gas supply system and configured to supply the sterilization gas from the sterilization gas generator to the external chamber.

With the above configuration, the sterilization efficiency for the external chamber can be improved during reducing equipment cost.

BRIEF DESCRIPTION OF THE DRAWINGS

FIG. 3B is a front view and FIG. 3A is a cross sectional view taking along the line A-A' in FIG. 3B.

FIGS. 12A and 12B are diagrams illustrating an external appearance of an isolator system according to another embodiment of the present invention. FIG. 12B is a front view and FIG. 12A is a cross sectional view taking along the line B-B' in FIG. 12A.

FIGS. 13A and 13B are diagrams illustrating an external appearance of an isolator system according to still another embodiment of the present invention. FIG. 13B is a front view and FIG. 13A is a cross sectional view taking along the line B-B' in FIG. 13A.

DETAILED DESCRIPTION OF THE EMBODIMENTS

Configuration of Sterilizer

Figure 1:
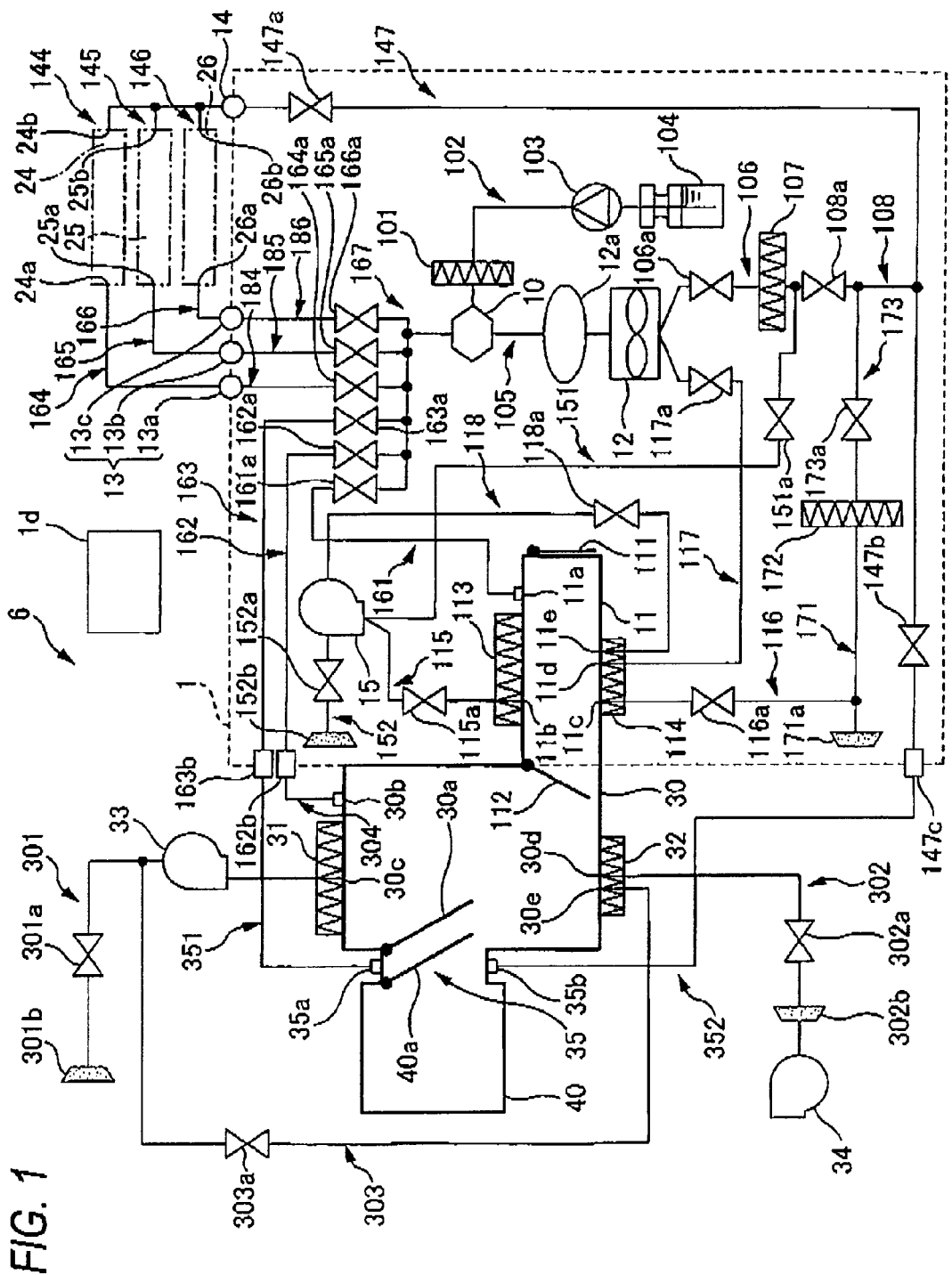
FIG. 1 is a system diagram illustrating an isolator system including a sterilizer according to an embodiment of the present invention.
Figure 2:
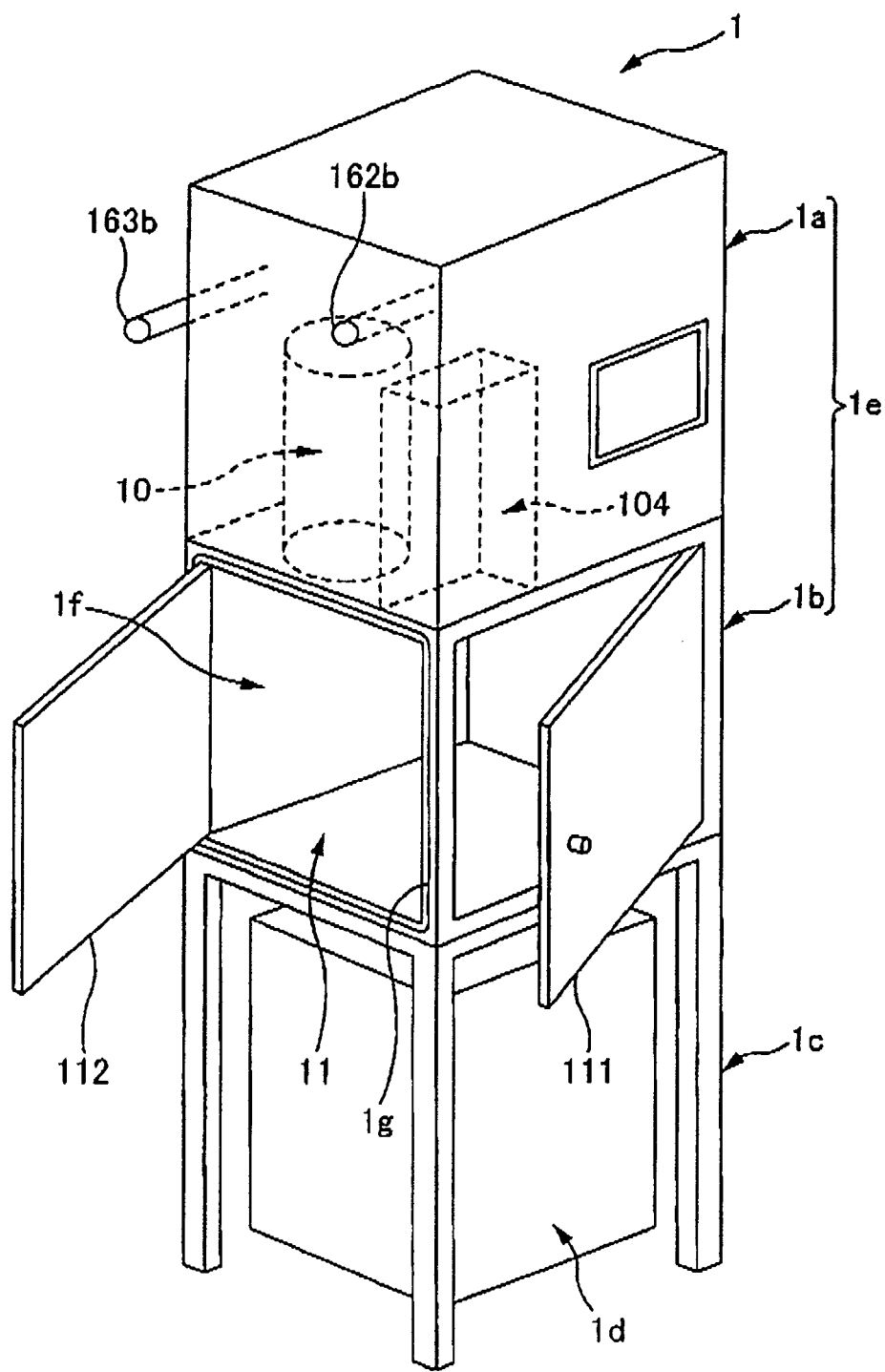
FIG. 2 is a perspective view illustrating an external appearance of the sterilizer according to the embodiment.
Figure 3A:
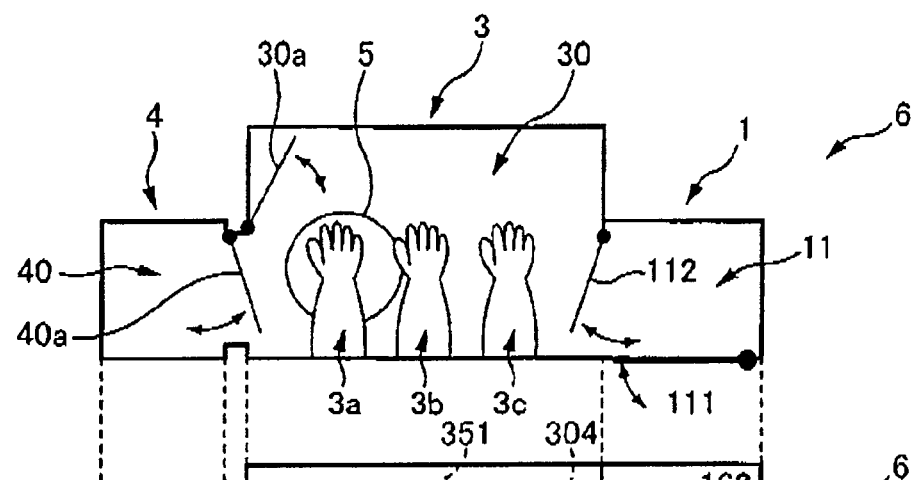
FIGS. 3A and 3B are diagrams illustrating an external appearance of the isolator system according to the embodiment.
Figure 3B:
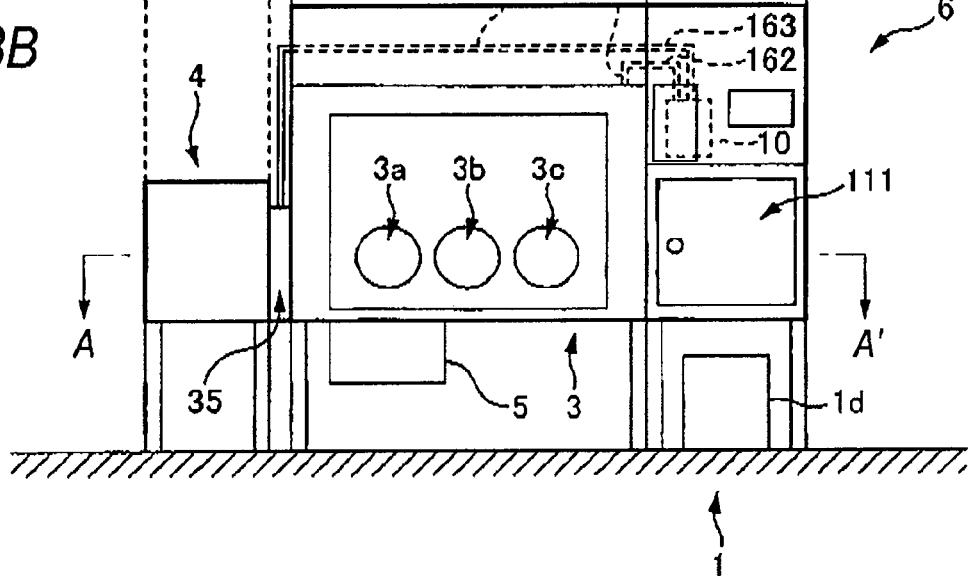

A configuration of a sterilizer 1 according to this exemplary embodiment will be described with reference to FIGS. 1 to 3. FIG. 1 is a system diagram illustrating an isolator system 6 including a sterilizer 1. FIG. 2 is a perspective view illustrating an external appearance of the sterilizer 1. FIGS. 3A and 3B are diagrams illustrating an external appearance of the isolator system 6. FIG. 3B is a front view and FIG. 3A is a cross sectional view taking along the line A-A' in FIG. 3B.

<Sterilization Chamber, and Outlet and Inlet Ports to Op Chamber>

As shown in FIG. 1, the sterilizer 1 includes a sterilization gas generator 10 and a sterilization chamber 11. The sterilization chamber 11 has a first door 111 for transferring a sterilization target article therethrough. The sterilizer 1 further includes outlet ports 13a, 13b and 13c (hereinafter, also referred to as "outlet ports 13") for supplying sterilization gas to three microscope chambers (external chambers) 24, 25 and 26 (hereinafter, referred to as "Op chambers 24, 25 and 26) therethrough, an inlet port 14 for inputting the sterilization gas from the Op chambers 24, 25, and 26 therethrough, and means, such as pipes, for circulating the sterilization gas into the sterilization chamber 11 and the Op chambers 24, 25, and 26.

The means for circulating the sterilization gas into the sterilization chamber 11 includes pipes 167, 161, 117, and 105, solenoid valves 161a and 117a, and a blower 12. Specifically, the gas outflow side (the upper side in FIG. 1) of the sterilization gas generator 10 is branched into solenoid valves 161a, 162a, 163a, 164a, 165a, and 166a by the pipe 167. Of these, the solenoid valve 161a and a sterilization gas feeding port 11a of the sterilization chamber 11 are connected to each other by the pipe 161. A sterilization gas discharging port 11d of the sterilization chamber 11 and the gas inflow side (the lower side in FIG. 1) of the blower 12 are connected to each other through the solenoid valve 117a by the pipe 117, and the gas outflow side (the upper side in FIG. 1) of the blower 12 and the gas inflow side (the lower side in FIG. 1) of the sterilization gas generator 10 are connected to each other through a flowmeter 12a by the pipe 105. With this configuration, the sterilization gas is supplied into the sterilization chamber 11 through the sterilization gas feeding port 11a, and is discharged outside the chamber 11 through the sterilization gas discharging port 11d. The configuration for circulating the sterilization gas into the sterilization chamber 11 corresponds to a first gas supply system. A filter 114, such as a HEPA filter, is provided directly downstream of the sterilization gas discharging port 11d of the sterilization chamber 11 so as to collect particulates. In this embodiment, "circulation of the sterilization gas" into the chambers such as the sterilization chamber 11 means that, in a repetitive manner, air containing the sterilization gas generated by the sterilization gas generator 10 is supplied to a chamber, air containing residual sterilization gas after the chamber is sterilized is discharged outside the chamber, discharged air is mixed with the sterilization gas generated by the sterilization gas generator 10, and air mixed with sterilization gas is supplied again into the chamber.

The means for circulating sterilization gas into the Op chambers 24, 25, and 26 includes pipes 167, 184, 185, 186, 164, 165, 166, 144, 145, 146, 147, 108, 106, and 105, solenoid valves 164a, 165a, 166a, 147a, 108a, and 106a, and the blower 12. Specifically, the gas outflow side (the upper side in FIG. 1) of the sterilization gas generator 10 is branched into the solenoid valves 161a, 162a, 163a, 164a, 165a, and 166a by the pipe 167. Of these, for example, the solenoid valve 164a and the outlet port 13a are connected to each other by the pipe 184, and the outlet port 13a and a gas feeding port 24a of the Op chamber 24 are connected to each other by the pipe 164. A gas discharging port 24b of the Op chamber 24 and the inlet port 14 are connected to each other by the pipe 144, and the inlet port 14 and the gas inflow side (the lower side in FIG. 1) of the blower 12 are connected to each other through the solenoid valves 147a, 108a, and 106a by the pipes 147, 108, and 106. The gas outflow side (the upper side in FIG. 1) of the blower 12 and the gas inflow side (the lower side in FIG. 1) of the sterilization gas generator 10 are connected to each other through the flowmeter 12a by the pipe 105. With this configuration, the sterilization gas is supplied into the Op chamber 24 through the gas feeding port 24a, and is discharged outside the Op chamber 24 through the gas discharging port 24b. As shown in FIG. 1, the same is applied to gas feeding ports 25a and 26a and gas discharging ports 25b and 26b of the Op chambers 25 and 26, and the solenoid valves 165a and 166a, the outlet ports 13b and 13c, the pipes 185 and 186, the pipes 165 and 166, and the pipes 145 and 146 corresponding to the chambers 25 and 26. The configuration for circulating the sterilization gas into the Op chambers 24, 25, and 26 corresponds to a second gas supply system. A filter 107 is provided downstream of the inlet port 14, at the boundary of the pipe 108 and the pipe 106.

The sterilization gas generator 10 is provided with a container 104 which contains a raw material (for example, a hydrogen peroxide solution) of sterilization gas (for example, hydrogen peroxide gas: $H_2O_2$), a pump 103 which supplies the raw material from the container 104, and a pipe 102 which supplies the raw material to the sterilization gas generator 10 through a filter 101.

In this embodiment, the sterilizer 1 further includes a controller 1d which controls electrical devices, such as the sterilization gas generator 10, various solenoid valves, and various blowers.

<Second Door and Outlet Port for Cell Manipulation Chamber>

As shown in FIG. 1, the sterilizer 1 further includes an outlet port 162b for supplying the sterilization gas to a cell manipulation chamber (external chamber) 30 of an isolator 3 (see FIGS. 3A and 3B) therethrough, a second door 112, and means, such as pipes, for circulating the sterilization gas into the cell manipulation chamber 30.

The means for circulating the sterilization gas into the cell manipulation chamber 30 includes pipes 167, 162, 304, 117, and 105, the solenoid valves 162a and 117a, and the blower 12. Specifically, the gas outflow side (the upper side in FIG. 1) of the sterilization gas generator 10 is branched into the solenoid valves 161a, 162a, 163a, 164a, 165a, and 166a by the pipe 167. Of these, the solenoid valve 162a and the outlet port 162b are connected to each other by the pipe 162, and the outlet port 162b and a sterilization gas feeding port 30b of the cell manipulation chamber 30 are connected to each other by the pipe 304. The configuration to connect the sterilization gas discharging port 11d of the sterilization chamber 11 and the gas inflow side (the lower side in FIG. 1) of the sterilization gas generator 10 is as described with respect to the means for circulating the sterilization gas into the sterilization chamber 11.

With the configuration, the sterilization gas is supplied into the chamber 30 through the sterilization gas feeding port 30b of the cell manipulation chamber 30, passing through the second door 112, and is discharged outside the chamber 11 through the sterilization gas discharging port 11*d* of the sterilization chamber 11. The configuration for circulating the sterilization gas into the cell manipulation chamber 30 also corresponds to a second gas supply system.

The cell manipulation chamber 30 is a chamber which is isolated from external air so as to perform predetermined pretreatment, in a sterilized manner, on cells to be cultured in a cell cultivation chamber 40. The sterilization chamber 11 is a chamber (which is smaller than cell manipulation chamber 30) which is isolated from external air so as to sterilize cells or articles necessary for cultivation before they are brought in the cell manipulation chamber 30. The cell manipulation chamber 30 is connected to the sterilization chamber 11 through the second door 112 with no space therebetween.

The cell manipulation chamber 30 is provided with a door 30*a* which faces the second door 112 of the sterilization chamber 11 to bring out the sterilized articles to the cell cultivation chamber 40 (see FIGS. 3A and 3B).

The cell manipulation chamber 30 is also provided with, as means for substituting the sterilization gas remained in the chamber 30 with air through a gas feeding port 30*c* and a gas discharging port 30*d*, sterilization gas reduction catalysts 301*b* and 302*b*, pipes 301 and 302, and solenoid valves 301*a* and 302*a*, and blowers 33 and 34.

The cell manipulation chamber 30 is also provided with means, such as pipes, for circulating air of the blower 33 through a filter 31 provided directly upstream of the gas feeding port 30*c* and a filter 32 provided directly downstream of the gas discharging port 30*d* so as to sterilize the filters 31 and 32. This means includes a pipe 303 which connects the gas feeding port 30*c* to the gas discharging port 30*e* of the cell manipulation chamber 30 through the blower 33, and a solenoid valve 303*a* which is provided on the pipe 303.

In this embodiment, the pipe 167, the solenoid valve 162*a*, the pipe 162, and the outlet port 162*b* also correspond to a second gas supply system.

<Outlet and Inlet Ports to Connector>

As shown in FIG. 1, the sterilizer 1 includes an outlet port 163*b* for supplying the sterilization gas to a hollow connector (external chamber) 35 connecting the cell manipulation chamber 30 and the cell cultivation chamber 40 of an incubator 4 (see FIGS. 3A and 3B) therethrough, an inlet port 147*c* for inputting the sterilization gas from the connector 35 therethrough, and means, such as pipes, for circulating the sterilization gas into the connector 35.

The means for circulating the sterilization gas into the connector 35 includes pipes 167, 163, 351, 352, 147, 108, 106, and 105, solenoid valves 163*a*, 147*b*, 108*a*, and 106*a*, and the blower 12. Specifically, the gas outflow side (the upper side in FIG. 1) of the sterilization gas generator 10 is branched into the solenoid valves 161*a*, 162*a*, 163*a*, 164*a*, 165*a*, and 166*a* by the pipe 167. Of these, the solenoid valve 163*a* and the outlet port 163*b* are connected to each other by the pipe 163, and the outlet port 163*b* and the gas feeding port 35*a* of the connector 35 are connected to each other by the pipe 351. The gas discharging port 35*b* of the connector 35 and the inlet port 147*c* are connected to each other by the pipe 352, the inlet port 147*c* and the gas inflow side (the lower side in FIG. 1) of the blower 12 are connected to each other through the solenoid valves 147*b*, 108*a*, and 106*a* by the pipes 147, 108, and 106, and gas outflow side (the upper side in FIG. 1) of the blower 12 and the gas inflow side (the lower side in FIG. 1) of the sterilization gas generator 10 are connected to each other through the flowmeter 12*a* by the pipe 105.

With this configuration, the sterilization gas is supplied into the connector 35 through the gas feeding port 35*a*, and is discharged outside the connector 35 through the gas discharging port 35*b*. The configuration for circulating the sterilization gas into the connector 35 also corresponds to a second gas supply system.

The cell cultivation chamber 40 of the incubator 4 is connected to the cell manipulation chamber 30 through the hollow connector 35 with no space therebetween. The cell cultivation chamber 40 is provided with a door 40*a* which faces the door 30*a* of the cell manipulation chamber 30 when being connected to the chamber 30 so as to bring the sterilized articles therein (see FIGS. 3A and 3B).

In this embodiment, the pipe 167, the solenoid valve 163*a*, the pipe 163, and the outlet port 163*b* also correspond to a second gas supply system.

<Configuration for Substituting Sterilization gas in Sterilization and Op Chambers with Air>

As shown in FIG. 1, the sterilizer 1 is also provided with a blower 15, a filter 113 which is provided directly upstream of the gas feeding port 11*b* of the sterilization chamber 11, means, such as pipes, for substituting the sterilization gas remained in the sterilization chamber 11 with air, and means, such as pipes, for substituting the sterilization gas remained in the Op chambers 24, 25, and 26 with air.

The means for substituting the residual sterilization gas in the sterilization chamber 11 with air includes pipes 152, 115, 116, and 171, and solenoid valves 152*a*, 115*a*, and 116*a*. The configuration for substituting the sterilization gas remained in the sterilization chamber 11 with air corresponds to a substitution system.

The means, such as pipes, for substituting the sterilization gas remained in the Op chambers 24, 25, and 26 with air includes pipes 152, 151, 106, 105, 167, 184, 185, 186, 164, 165, 166, 144, 145, 146, 147, 108, 173, and 171, and solenoid valves 152*a*, 151*a*, 106*a*, 164*a*, 165*a*, 166*a*, 147*a*, and 173*a*. The configuration for substituting the sterilization gas remained in the Op chambers 24, 25, and 26 with air also correspond to a substitution system.

A sterilization gas reduction catalyst 152*b* is provided at an atmosphere-side opening end of the pipe 152, and a sterilization gas reduction catalyst 171*a* is provided at an atmosphere-side opening end of the pipe 171.

<Configuration for Sterilizing Filter>

As shown in FIG. 1, the sterilizer 1 includes means, such as pipes, for circulating air of the blower 15 through the filters 113 and 114 so as to sterilize the filters 113 and 114. This means includes pipes 118 and 115, and solenoid valves 115*a* and 118*a*.

<External Appearance Configuration Example>

As shown in FIG. 2, the sterilizer 1 includes a central portion 1*b* provided with the sterilization chamber 11, an upper portion 1*a* which is provided above the central portion 1*b* in the vertical direction so as to accommodate the sterilization gas generator 10 and the like, a lower portion 1*c* which is provided below the central portion 1*b* in the vertical direction so as to function as a mount, and the controller 1*d* which is provided in a space defined by the lower portion 1*c*.

In this embodiment, the upper portion 1*a* and the lower portion 1*b* constitute a housing 1*e*. Accommodated in the upper portion 1*a* are a container 104 which contains the raw material of the sterilization gas, such as a hydrogen peroxide solution, the sterilization gas generator 10, and the like. The upper portion 1*a* is provided with the above-described outlet port 162*b* for supplying the sterilization gas to the cell manipulation chamber 30 therethrough, and the above-described outlet port 163*b* for supplying the sterilization gas to the connector 35 therethrough. A side of the central portion 1*b*, on which the second door 112 is provided functions as a connecting portion to the isolator 3. A predetermined seal member 1g is provided around an opening 1f which the second door 112 opens/closes. The ports 13, 14, and 147c are not shown.

As shown in FIGS. 3A and 3B, the sterilization chamber 11 of the sterilizer 1 and one side (the right side in FIGS. 3A and 3B) of the cell manipulation chamber 30 of the isolator 3 are connected to each other through the second door 112 of the sterilization chamber 11 with no space therebetween.

The other side (the left side in FIGS. 3A and 3B) of the cell manipulation chamber 30 of the isolator 3 and the cell cultivation chamber 40 of the incubator 4 are connected to each other through the hollow connector 35, the door 30a of the cell manipulation chamber 30 and the door 40a of the cell cultivation chamber 40 with no space therebetween.

The cell manipulation chamber 30 is provided with, for example, globes 3a, 3b, and 3c and a centrifuge 5. For example, the door 30a can be opened/closed by using globe 3a in a state where the cell manipulation chamber 30 is maintained to be sterilized. The second door 112 can be opened/closed by using the globe 3c in a state where the sterilization chamber 11 is maintained to be sterilized.

From the sterilization gas generator 10 of the sterilizer 1, the sterilization gas is supplied to the cell manipulation chamber 30 through the pipes 162 and 304, and the sterilization gas is supplied to the connector 35 through the pipes 163 and 351.

In this embodiment, the isolator 3 and the sterilizer 1 constitute the isolator system 6.

(Operation of Sterilizer)

Figure 4:
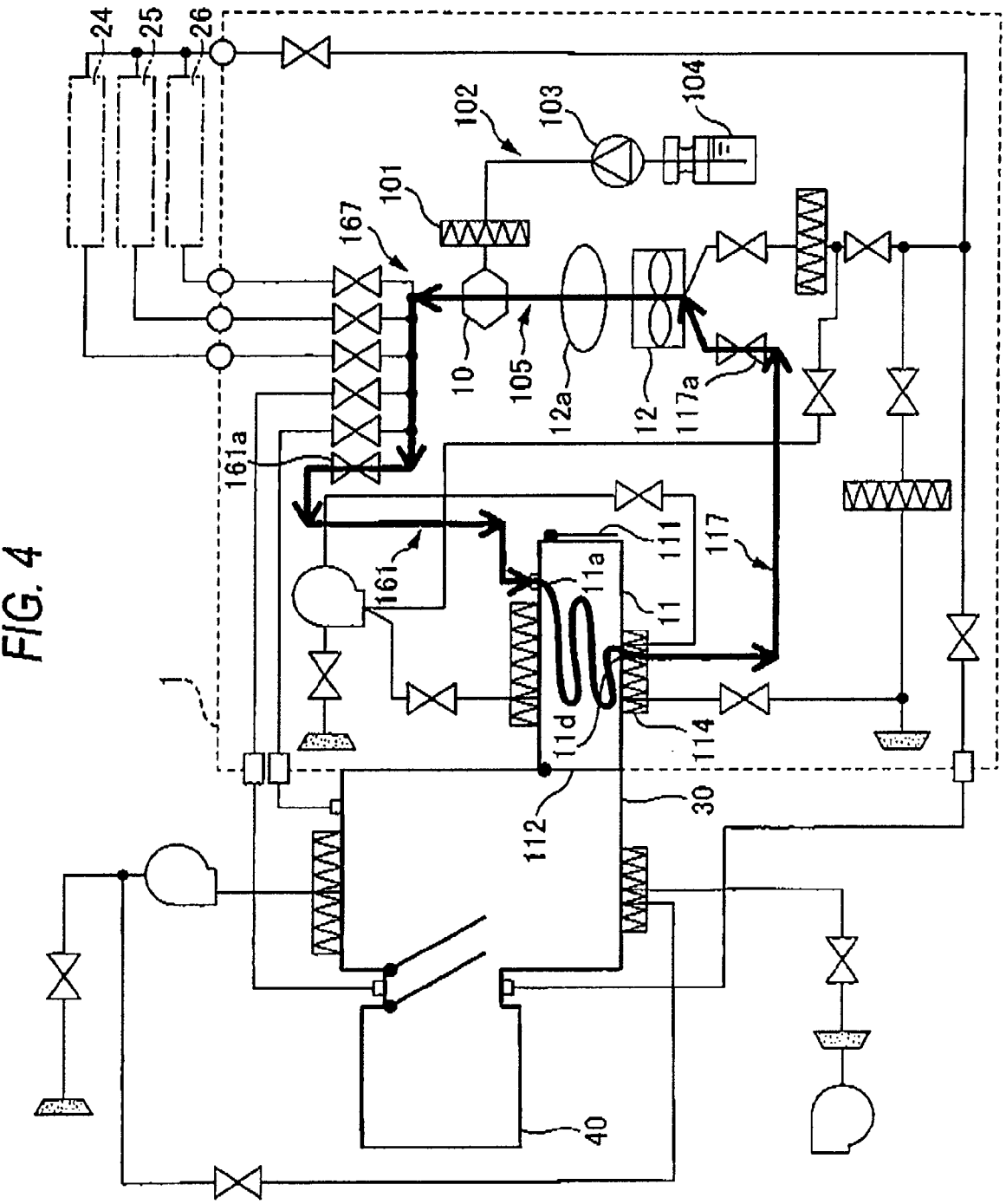
FIG. 4 is a system diagram illustrating a flow of sterilization gas in a sterilization process of a sterilization chamber according to the embodiment.
Figure 5:
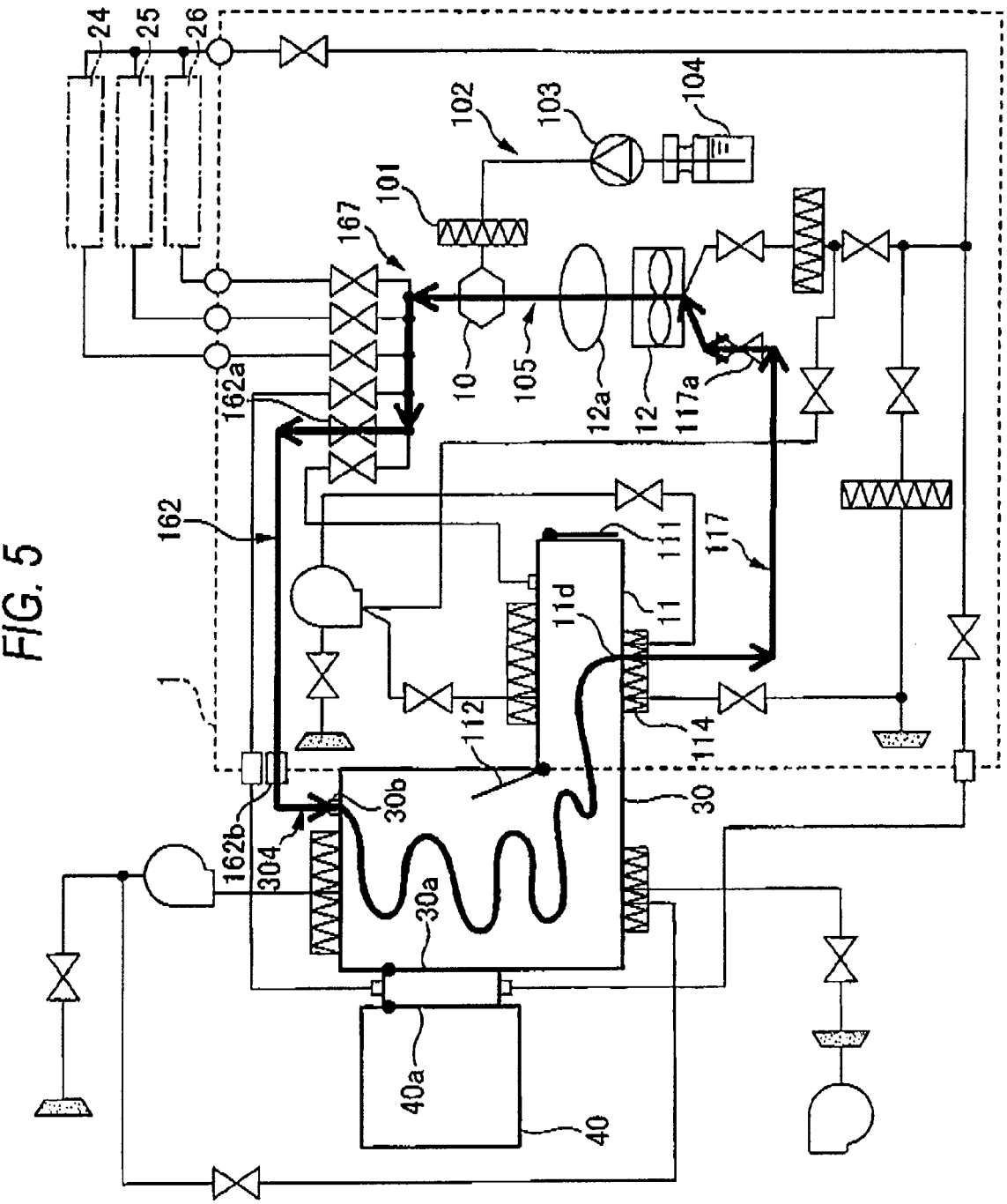
FIG. 5 is a system diagram illustrating a flow of sterilization gas in a sterilization process of the sterilization chamber and a cell manipulation chamber according to the embodiment.
Figure 6:
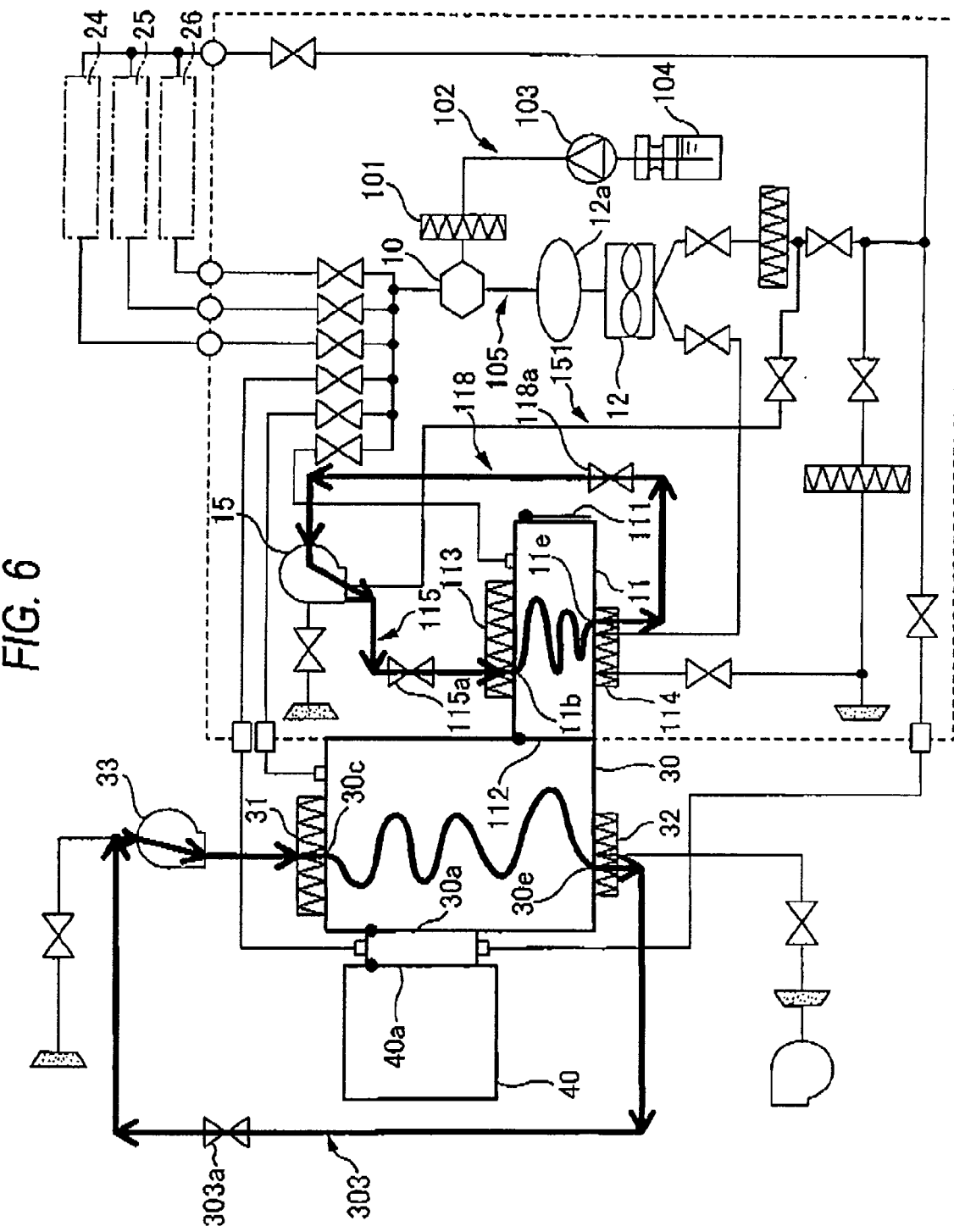
FIG. 6 is a system diagram illustrating a flow of sterilization gas in a sterilization process of filters for the sterilization chamber and a flow of sterilization gas in a sterilization process of filters for the cell manipulation chamber according to the embodiment.
Figure 7:
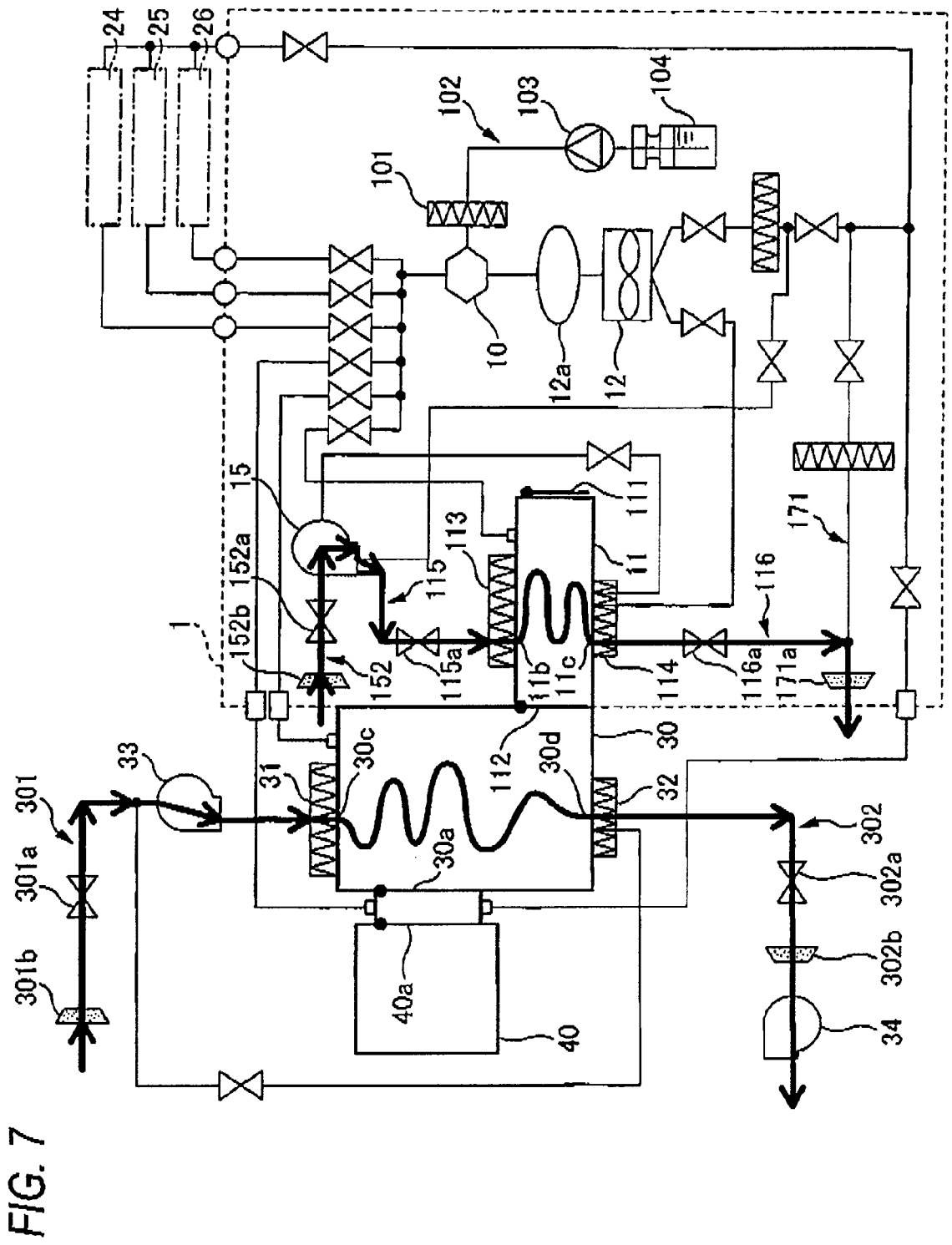
FIG. 7 is a system diagram illustrating a flow of air in a substitution process of the sterilization chamber and a flow of air in a substitution process of the cell manipulation chamber according to the embodiment.
Figure 8:
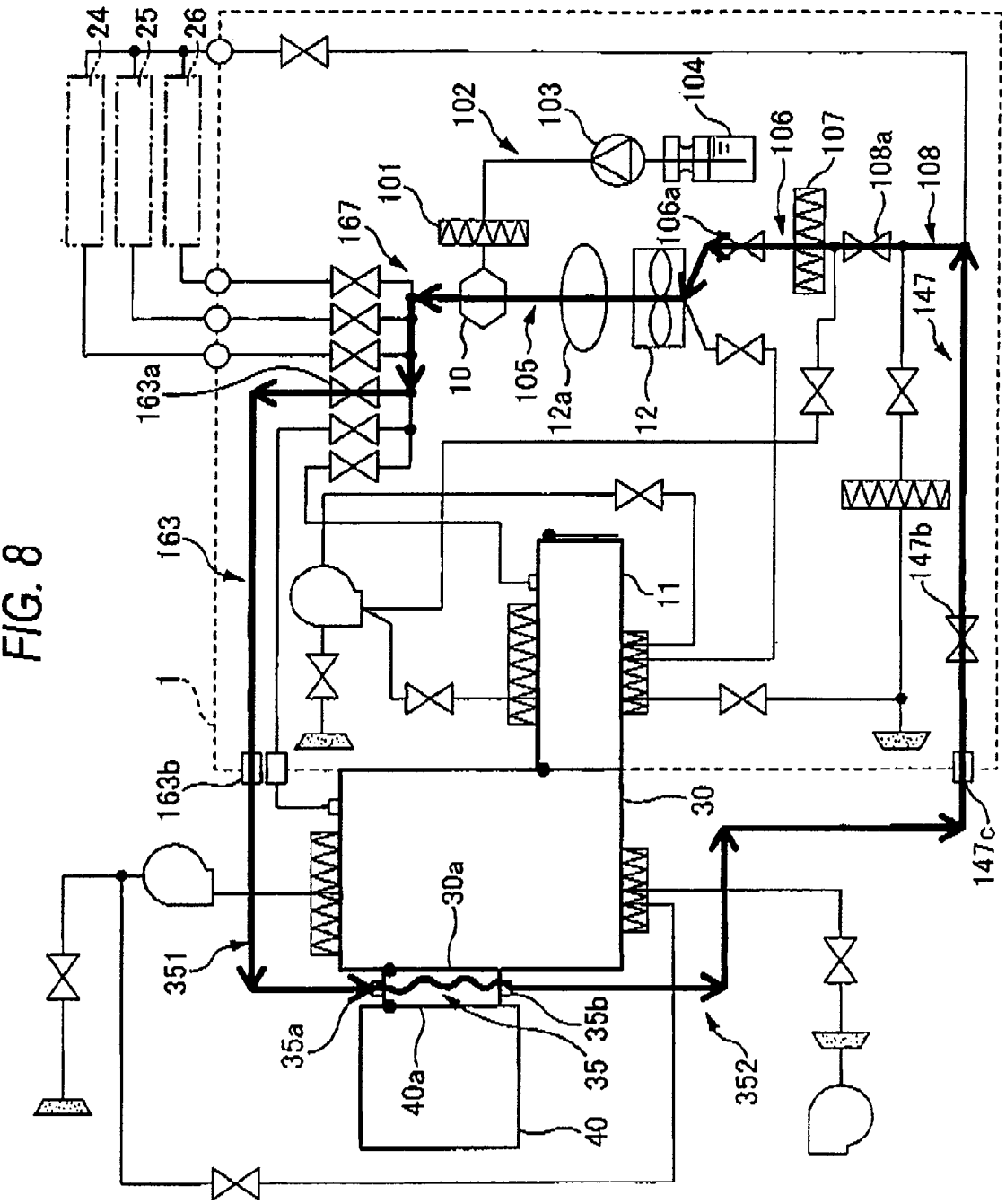
FIG. 8 is a system diagram illustrating a flow of sterilization gas in a sterilization process of a connector according to the embodiment.
Figure 9:
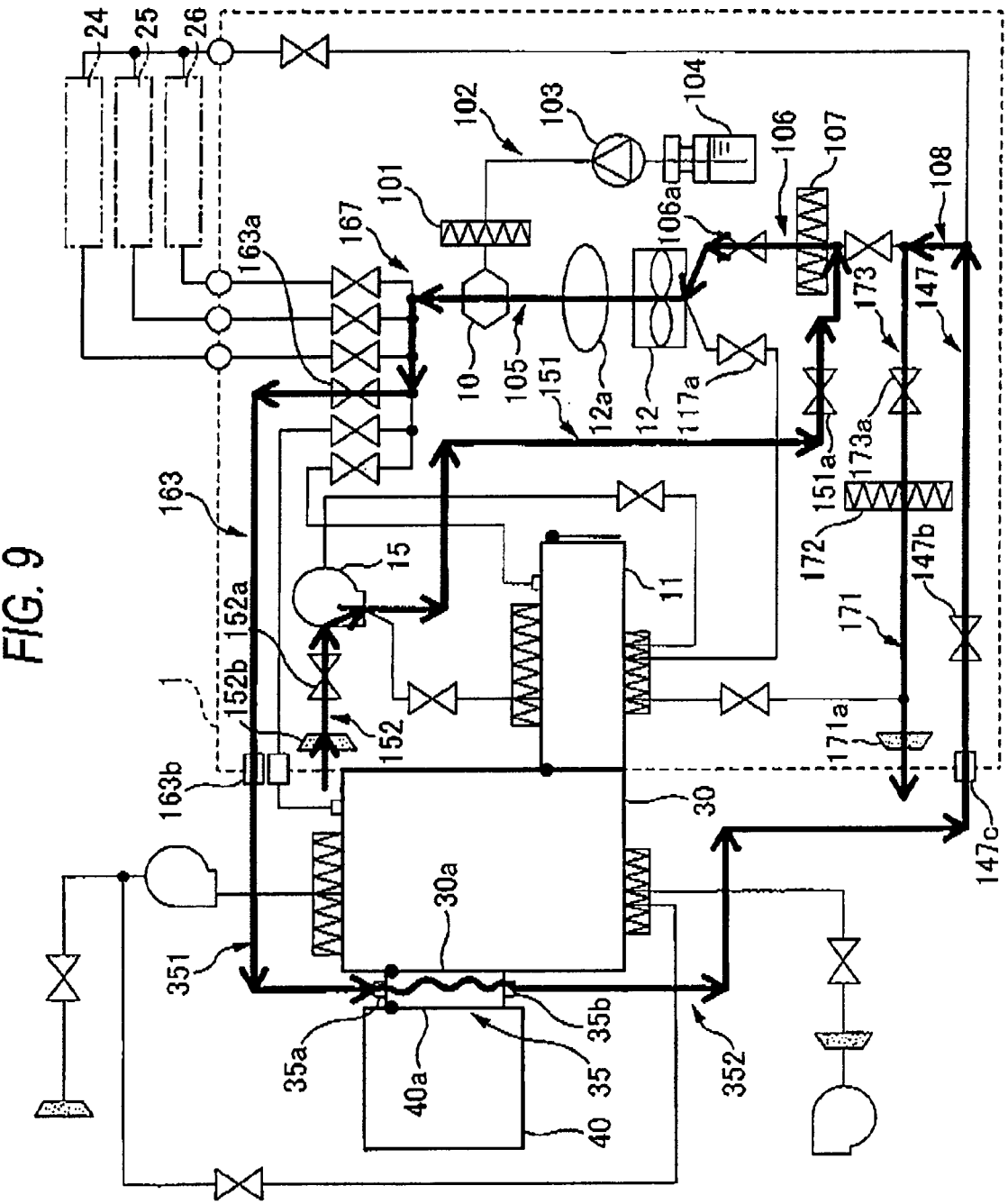
FIG. 9 is a system diagram illustrating a flow of air in a substitution process of the connector according to the embodiment.
Figure 10:
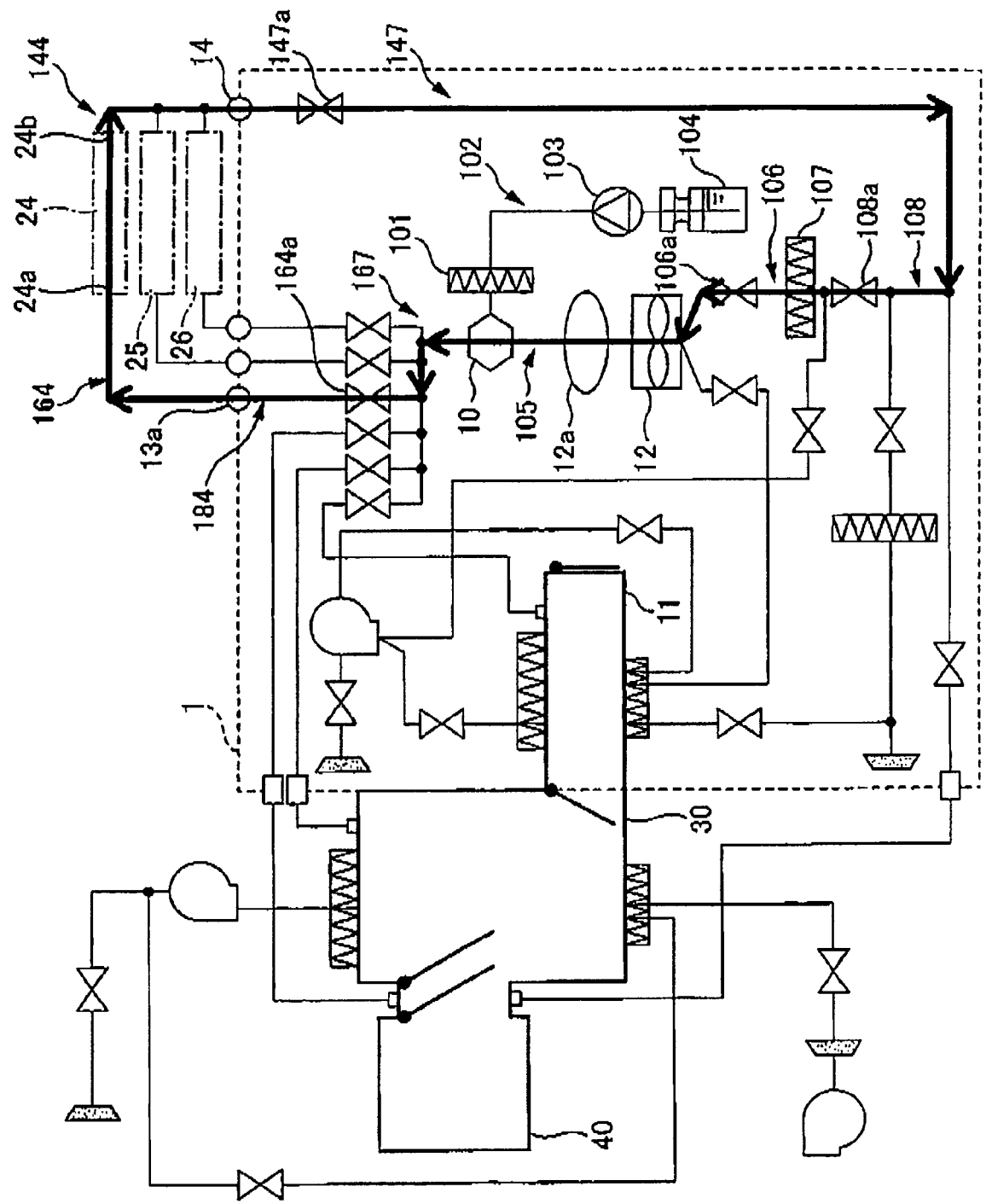
FIG. 10 is a system diagram illustrating a flow of sterilization gas in a sterilization process of an Op chamber and a flow of sterilization gas in a sterilization process of a filter according to the embodiment.
Figure 11:
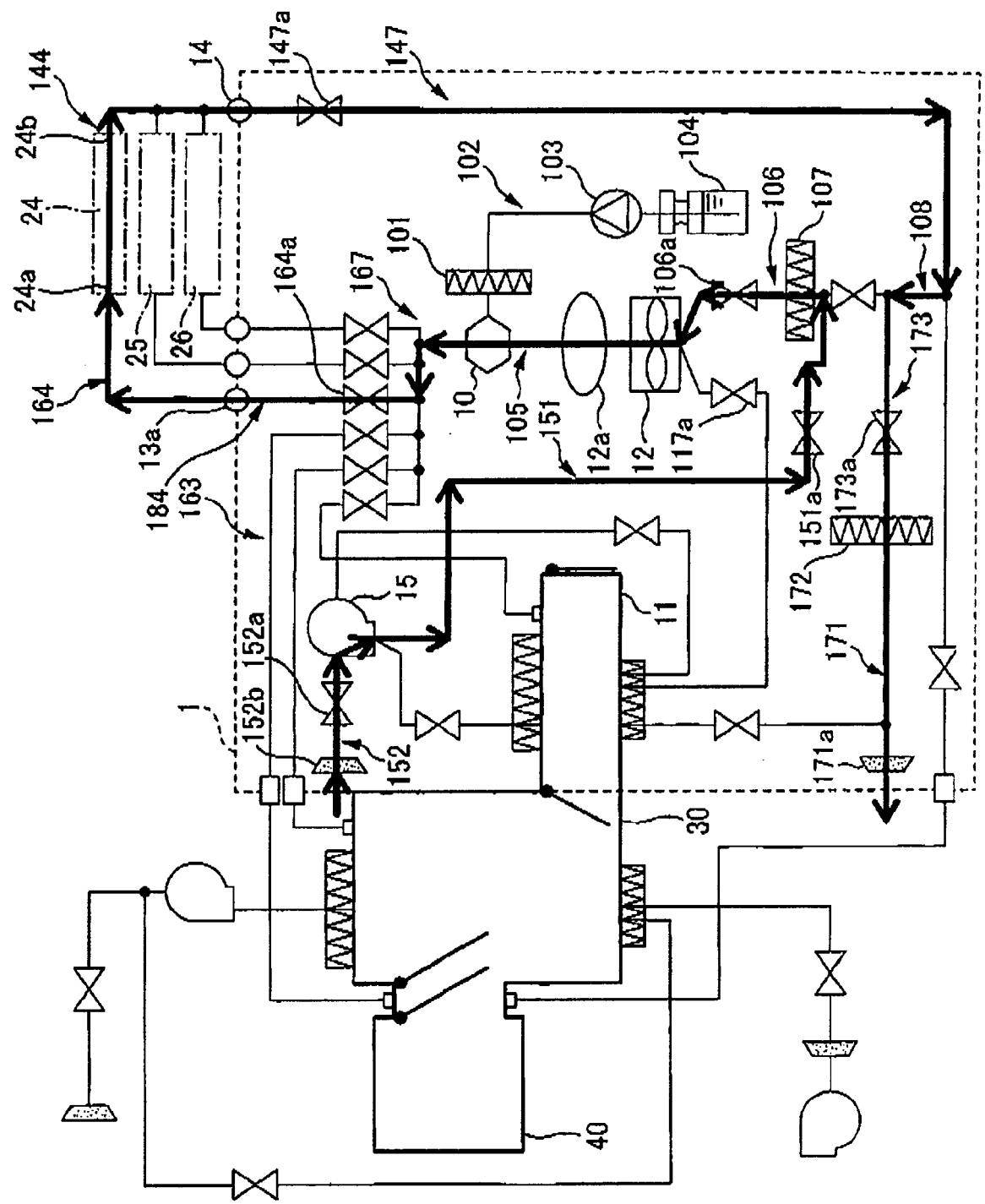
FIG. 11 is a system diagram illustrating a flow of air in a substitution process of the Op chamber according to the embodiment.

The operations of the sterilization process and the substitution process by the sterilizer 1 configured as above will be described with reference to FIGS. 4 to 11. FIG. 4 is a system diagram illustrating a flow of sterilization gas in a sterilization process of the sterilization chamber 11. FIG. 5 is a system diagram illustrating a flow of sterilization gas in a sterilization process of the sterilization chamber 11 and the cell manipulation chamber 30. FIG. 6 is a system diagram illustrating a flow of sterilization gas in a sterilization process of the filters 113 and 114 for the sterilization chamber 11 and a flow of sterilization gas in a sterilization process of the filters 31 and 32 for the cell manipulation chamber 30. FIG. 7 is a system diagram illustrating a flow of air in a substitution process of the sterilization chamber 11 and a flow of air in a substitution process of the cell manipulation chamber 30. FIG. 8 is a system diagram illustrating a flow of sterilization gas in a sterilization process of the connector 35. FIG. 9 is a system diagram illustrating a flow of air in a substitution process of the connector 35. FIG. 10 is a system diagram illustrating a flow of sterilization gas in a sterilization process of the Op chamber 24 and a flow of sterilization gas in a sterilization process of the filter 107. FIG. 11 is a system diagram illustrating a flow of air in a substitution process of the Op chamber 24.

In FIGS. 4 and 11, for convenience, only the elements directly related to the flows of the sterilization gas or the air indicated by bold lines are represented by reference numerals. The reference numerals of the members are the same as the reference numerals in FIG. 1.

<Exposure Process of Sterilization Chamber>

As indicated by a bold arrow of FIG. 4, first, in a state where the first door 111 and the second door 112 of the sterilization chamber 11 are closed, the sterilization gas passes through the sterilization gas generator 10, the pipe 167, the solenoid valve 161a, and the pipe 161, and is supplied from the sterilization gas feeding port 11a into the sterilization chamber 11. Next, air (this is also referred to as "sterilization gas") containing residual sterilization gas after sterilization in the sterilization chamber 11 is discharged from the sterilization gas discharging port 11d outside the sterilization chamber 11, passes through the filter 114, the pipe 117, the solenoid valve 117a provided in the pipe 117, the blower 12, the pipe 105, and the flowmeter 12a provided in the pipe 105, enters the sterilization gas generator 10, and is mixed with sterilization gas newly generated by the generator 10. In FIG. 4, in order to form the flow of the sterilization gas indicated by the bold arrow, the open/close states of various solenoid valves are set by the controller 1d.

The flow of the sterilization gas is formed by the blower 12. In the sterilization process, the sterilization gas generator 10 generates sterilization gas (for example, hydrogen peroxide gas) from a raw material (for example, hydrogen peroxide solution) of sterilization gas supplied from the container 104 by the pump 103.

<Sterilization Process of Cell Manipulation Chamber>

As indicated by the bold arrow of FIG. 5, in a state where the first door 111 of the sterilization chamber 11 and the door 30a of the cell manipulation chamber 30 are closed, and the second door 112 of the sterilization chamber 11 is opened, the sterilization gas first passes through the sterilization gas generator 10, the pipe 167, the solenoid valve 162a, the pipe 162, the outlet port 162b, and the pipe 304, and is supplied from the sterilization gas feeding port 30b into the cell manipulation chamber 30. Next, air (this is also referred to as "sterilization gas") containing residual sterilization gas after sterilization in the cell manipulation chamber 30 is supplied to the sterilization chamber 11 in a state where the second door 112 is opened, is discharged from the sterilization gas discharging port 11d outside the chamber 11, passes through the filter 114, the pipe 117, the solenoid valve 117a provided in the pipe 117, the blower 12, the pipe 105, and the flowmeter 12a provided in the pipe 105, enters the sterilization gas generator 10, and is mixed with sterilization gas newly generated by the generator 10. In FIG. 5, in order to form the flow of the sterilization gas indicated by the bold arrow, the open/close states of various solenoid valves are set by the controller 1d. The sterilization gas after sterilization in the cell manipulation chamber 30 can also sterilize the sterilization chamber 11. That is, the sterilization gas supplied to the cell manipulation chamber 30 through the sterilization gas feeding port 30b sterilizes the chamber 30, is supplied from the opened second door 112 to the sterilization chamber 11 to sterilize the chamber 11, and is discharged from the sterilization gas discharging port 11d. Thus, when the cell manipulation chamber 30 is sterilized, the sterilization chamber 11 is also sterilized.

The above-described flow of the sterilization gas is formed by the blower 12. In the sterilization process, the sterilization gas generator 10 generates sterilization gas (for example, hydrogen peroxide gas) from the raw material of sterilization gas (for example, hydrogen peroxide solution) supplied from the container 104 by the pump 103.

Thus, the sterilization gas from the sterilizer 1 is directly introduced into the cell manipulation chamber 30 of the isolator 3 through the outlet port 162b, so the chamber 30 can be efficiently sterilized. Therefore, the time required for sterilization can be shortened. In addition, the isolator 3 should not be provided with the sterilizing means separately, so equipment cost can be reduced as much.

<Sterilization Process of Filter for Sterilization Chamber and Cell Manipulation Chamber>

As indicated by a bold arrow on the right side in FIG. 6, in a state where the first door 111 and the second door 112 of the sterilization chamber 11 are closed, air first passes through the blower 15, the pipe 115, the solenoid valve 115a provided in the pipe 115, and the filter 113, and is supplied from the gas feeding port 11b into the sterilization chamber 11. Next, air is discharged from the gas discharging port 11e outside the sterilization chamber 11, passes through the filter 114, the pipe 118, and the solenoid valve 118a provided in the pipe 118, and returns to the blower 15. In FIG. 6, in order to form the flow of the air indicated by the bold arrow, the open/close states of various solenoid valves are set by the controller 1d. The above-described flow of air is formed by the blower 15. At the time of such circulation of air, the flow of the sterilization gas for sterilization of the sterilization chamber 11 shown in FIG. 4 may be formed together. Alternatively, at the time of such circulation of air, the sterilization gas may remain in the sterilization chamber 11 after the sterilization process shown in FIG. 4 ends.

As indicated by a bold arrow on the left side in FIG. 6, in a state where the door 30a of the cell manipulation chamber 30, and the first door 111 and the second door 112 of the sterilization chamber 11 are all closed, air first passes through the blower 33, the pipe 303, and the filter 31, and is supplied from the gas feeding port 30c into the cell manipulation chamber 30. Next, air is discharged from the gas discharging port 30e outside the cell manipulation chamber 30, passes through the filter 32, the pipe 303, and the solenoid valve 303a provided in the pipe 303, and returns to the blower 33. In FIG. 6, in order to form the flow of the air indicated by the bold arrow, the open/close states of various solenoid valves are set by the controller 1d. The above-described flow of air is formed by the blower 33. At the time such circulation of air, the flow of the sterilization gas for sterilization of the sterilization chamber 11 and the cell manipulation chamber 30 shown in FIG. 5 may be formed together. Alternatively, at the time of such circulation of air, the sterilization gas may remain in the sterilization chamber 11 and the cell manipulation chamber 30 after the sterilization process shown in FIG. 5 ends.

In the sterilization process, the sterilization gas generator 10 generates sterilization gas (for example, hydrogen peroxide gas) from the raw material of sterilization gas (for example, hydrogen peroxide solution) supplied from the container 104 by the pump 103.

Although in the above-described example, the sterilization process of the filters 113 and 114 of the sterilization chamber 11 and the sterilization process of the filters 31 and 32 of the cell manipulation chamber 30 are performed separately, the invention is not limited thereto. For example, in a state where the second door 112 is opened, both processes may be performed simultaneously. The filters 113 and 114 of the sterilization chamber 11 and the filters 31 and 32 of the cell manipulation chamber 30 are sterilized simultaneously, such that the sterilization processing of the filters 113, 114, 31, and 32 of the chambers 11 and 30 is synergistically performed, and thus the sterilization effect is improved.

Therefore, the insides of the sterilization chamber 11 and the cell manipulation chamber 30 can be reliably sterilized.

<Substitution Process of Sterilization Chamber and Cell Manipulation Chamber>

After the sterilization processes of the sterilization chamber 11, the cell manipulation chamber 30, and the filters 113, 114, 31, and 32 shown in FIGS. 4 to 6, a process for substituting the residual sterilization gas with air in the atmosphere is performed.

As indicated by a bold arrow on the right side in FIG. 7, in a state where the first door 111 and the second door 112 of the sterilization chamber 11 are closed, air in the atmosphere first passes through the sterilization gas reduction catalyst 152b, the pipe 152, the solenoid valve 152a provided in the pipe 152, the blower 15, the pipe 115, the solenoid valve 115a provided in the pipe 115, and the filter 113, and is supplied from the gas feeding port 11b into the sterilization chamber 11. Next, air is discharged from the gas discharging port 11e outside the sterilization chamber 11, passes through the filter 114, the pipe 116, the solenoid valve 116a provided in the pipe 116, the pipe 171, and the sterilization gas reduction catalyst 171a, and is emitted to the atmosphere. In FIG. 7, in order to form the flow of air indicated by the bold arrow on the right side, the open/close states of various solenoid valves are set by the controller 1d. The above-described flow of air is formed by the blower 15.

As indicated by a bold arrow on the left side in FIG. 7, in a state where the door 30a of the cell manipulation chamber 30, and the first door 111 and the second door 112 of the sterilization chamber 11 are all closed, air in the atmosphere first passes through the sterilization gas reduction catalyst 301b, the pipe 301, the solenoid valve 301a provided in the pipe 301, the blower 33, and the filter 31, and is supplied from the gas feeding port 30c into the cell manipulation chamber 30. Next, air is discharged from the gas discharging port 30d outside the cell manipulation chamber 30, passes through the filter 32, the pipe 302, the solenoid valve 302a provided in the pipe 302, the sterilization gas reduction catalyst 302b, and the blower 34, and is emitted to the atmosphere. In FIG. 7, in order to form the flow of air indicated by the bold arrow on the left side, the open/close states of various solenoid valves are set by the controller 1d. The above-described flow of air is formed by the blowers 33 and 34.

Although in the above-described example, the substitution process of the sterilization chamber 11 and the substitution process of the cell manipulation chamber 30 are performed separately, the invention is not limited thereto. For example, in a state where the second door 112 is opened, both processes may be performed simultaneously. The substitution processes of the sterilization chamber 30 and the cell manipulation chamber 11 are performed simultaneously, such that the sterilization gas is synergistically removed from the chambers 11 and 30, and thus the removal effect of the sterilization gas is improved.

Therefore, after the sterilization process, the sterilization gas which affects the cells or the like can be reliably removed from the insides of the sterilization chamber 11 and the cell manipulation chamber 30.

<Sterilization Process of Connector>

As indicated by a bold arrow of FIG. 8, in a state where the door 30a of the cell manipulation chamber 30 and the door 40a of the cell cultivation chamber 40, which sandwiches the hollow connector 35 are closed, the sterilization gas passes through the sterilization gas generator 10, the pipe 167, the solenoid valve 163a, the pipe 163, the outlet port 163b, and the pipe 351, and is supplied from the gas feeding port 35a into the connector 35. Next, air (this is also referred to as "sterilization gas") containing residual sterilization gas after sterilization in the connector 35 is discharged from the gas discharging port 35b outside the connector 35, passes through the pipe 352, the inlet port 147c, the pipe 147, the solenoid valve 147b provided in the pipe 147, the pipe 108, the solenoid valve 108a provided in the pipe 108, the filter 107, the pipe 106, the solenoid valve 106a provided in the pipe 106, the blower 12, the pipe 105, and the flowmeter 12a provided in the pipe 105, enters the sterilization gas generator 10, and is mixed with sterilization gas newly generated by the generator 10. In FIG. 8, in order to form the flow of the sterilization gas indicated by the bold arrow, the open/close states of various solenoid valves are set by the controller 1d.

The above-described flow of the sterilization gas is formed by the blower 12. In the sterilization process, the sterilization gas generator 10 generates sterilization gas (for example, hydrogen peroxide gas) from the raw material of sterilization gas (for example, hydrogen peroxide solution) supplied from the container 104 by the pump 103.

Therefore, the isolator 3 and the incubator 4 can be connected to each other while the chambers 30 and 40 are maintained in a sterile state.

<Substitution Process of Connector>

After the sterilization process of the connector 35 shown in FIG. 8, a process for substituting residual sterilization gas with air in the atmosphere is performed.

As indicated by a bold arrow of FIG. 9, in a state where the door 30a of the cell manipulation chamber 30 and the door 40a of the cell cultivation chamber 40, which sandwich the hollow connector 35 are closed, air in the atmosphere passes through the sterilization gas reduction catalyst 152b, the pipe 152, the solenoid valve 152a provided in the pipe 152, the blower 15, the pipe 151, the solenoid valve 151a provided in the pipe 151, the filter 107, the pipe 106, the solenoid valve 106a provided in the pipe 106, the blower 12, the pipe 105, the flowmeter 12a provided in the pipe 105, the sterilization gas generator 10, the pipe 167, the solenoid valve 163a, the pipe 163, the outlet port 163b, and the pipe 351, and is supplied from the gas feeding port 35a into the connector 35. Next, air is discharged from the gas discharging port 35b outside the connector 35, passes through the pipe 352, the inlet port 147c, the pipe 147, the solenoid valve 147b provided in the pipe 147, the pipe 108, the pipe 173, the solenoid valve 173a provided in the pipe 173, the filter 172, the pipe 171, and the sterilization gas reduction catalyst 171a, and is emitted to the atmosphere. In FIG. 9, in order to form the flow of air indicated by the bold arrow, the open/close states of various solenoid valves are set by the controller 1d. The above-described flow of air is formed by the blower 15.

In the substitution process, it is assumed that neither the raw material of sterilization gas (for example, a hydrogen peroxide solution) supplied from the container 104 nor the sterilization gas (for example, hydrogen peroxide gas) remain in the sterilization gas generator 10, and both the operation of the sterilization gas generator 10 to generate the sterilization gas from the raw material of sterilization gas and the operation of the pump 103 are stopped.

Therefore, after the sterilization process, the sterilization gas which affects the cells or the like can be reliably removed from the inside of the connector 35.

<Sterilization Process of Op Chamber and Sterilization Process of Filter>

For example, a process for sterilizing the Op chamber 24 by using the sterilizer 1 will be described.

As indicated by a bold arrow of FIG. 10, the sterilization gas first passes through the sterilization gas generator 10, the pipe 167, the solenoid valve 164a, the pipe 184, the outlet port 13a, and the pipe 164, and is supplied from the gas feeding port 24a into the Op chamber 24. Next, air (this is also referred to as "sterilization gas") containing residual sterilization gas after sterilization in the Op chamber 24 is discharged from the gas discharging port 24b outside the Op chamber 24, passes through the pipe 144, the inlet port 14, the pipe 147, the solenoid valve 147a provided in the pipe 147, the pipe 108, the solenoid valve 108a provided in the pipe 108, the filter 107, the pipe 106, the solenoid valve 106a provided in the pipe 106, the blower 12, the pipe 105, and the flowmeter 12a provided in the pipe 105, enters the sterilization gas generator 10, and is mixed with sterilization gas newly generated by the generator 10. In FIG. 10, in order to form the flow of the sterilization gas indicated by the bold arrow, the open/close states of various solenoid valves are set by the controller 1d. The above-described flow of the sterilization gas is formed by the blower 12.

The same is applied to the Op chambers 25 and 26.

In the process for sterilizing the filter 107, the flow of air is the same as the flow of the sterilization gas of FIG. 10. In this case, as described above, the flow of the sterilization gas may be formed together, or after the sterilization process by the sterilization gas ends, the sterilization gas may remain in the Op chambers 24, 25, and 26.

Therefore, the cells cultured by the incubator 4 or the articles necessary for cultivation can be sterilized by the sterilizer 1, and in the Op chambers 24, 25, and 26 which are not connected the sterilizer 1 through a door, the exterior of the article or the chambers can be sterilized. In addition, the Op chambers 24, 25, and 26 should not be provided with sterilizing means separately, so cost can be reduced as much.

<Substitution Process of Op Chamber>

After the sterilization process of the Op chamber 24 shown in FIG. 10, a process for substituting residual sterilization gas with air in the atmosphere is performed.

As indicated by a bold arrow of FIG. 11, air in the atmosphere passes through the sterilization gas reduction catalyst 152b, the pipe 152, the solenoid valve 152a provided in the pipe 152, the blower 15, the pipe 151, the solenoid valve 151a provided in the pipe 151, the filter 107, the pipe 106, the solenoid valve 106a provided in the pipe 106, the blower 12, the pipe 105, the flowmeter 12a provided in the pipe 105, the sterilization gas generator 10, the pipe 167, the solenoid valve 164a, the pipe 184, the outlet port 13a, and the pipe 164, and is supplied from the gas feeding port 24a into the Op chamber 24. Next, air is discharged from the gas discharging port 24b outside the Op chamber 24, passes through the pipe 144, the inlet port 14, the pipe 147, the solenoid valve 147a provided in the pipe 147, the pipe 108, the pipe 173, the solenoid valve 173a provided in the pipe 173, the filter 172, the pipe 171, and the sterilization gas reduction catalyst 171a, and is emitted to the atmosphere. In FIG. 11, in order to form the flow of air indicated by the bold arrow, the open/close states of various solenoid valves are set by the controller 1d. The above-described flow of air is formed by the blower 15.

In the above-described substitution process, it is assumed that neither the raw material of sterilization gas (for example, hydrogen peroxide solution) supplied from the container 104 nor the sterilization gas (for example, hydrogen peroxide gas) remains in the sterilization gas generator 10, and both the operation of the sterilization gas generator 10 to generate the sterilization gas from the raw material of sterilization gas and the operation of the pump 103 are stopped.

Therefore, after the sterilization process, the sterilization gas which affects the cells or the like can be reliably removed from the insides of the Op chambers 24, 25, and 26.

(Isolator Systems 6' and 6")

The isolator system of this embodiment is not limited to the isolator system 6 shown in FIGS. 3A and 3B, and it may be isolator systems 6' and 6" shown in FIGS. 12A and 12B and FIGS. 13A and 13B. FIGS. 12A and 12B are diagrams illustrating an external appearance of the isolator system 6'. FIG. 12B is a front view and FIG. 12A is a cross sectional view taking along the line B-B' in FIG. 12A. FIGS. 13A and 13B are diagrams illustrating an external appearance of the isolator system 6". FIG. 13B is a front view and FIG. 13A is a cross sectional view taking along the line B-B' in FIG. 13A.

With regard to elements shown in FIGS. 3A and 3B, FIGS. 12A and 12B, and FIGS. 13A and 13B, the same elements are represented by the same reference numerals, and detailed description thereof will not be repeated.

<Isolator System 6'>

The isolator system 6' shown in FIGS. 12A and 12B includes two isolators 3 and 3', and one sterilizer F. The sterilizer 1' includes second doors 112 and 112' on both sides adjacent to a first door 111 in a sterilization chamber 11'.

The sterilization chamber 11' of the sterilizer 1' and one side (the right side in FIGS. 12A and 12B) of the cell manipulation chamber 30 of the isolator 3 are connected to each other through the second door 112 of the sterilization chamber 11' with no space therebetween. The other side (the left side in FIGS. 12A and 12B) of the cell manipulation chamber 30 of the isolator 3 and the cell cultivation chamber 40 of the incubator 4 are connected to each other through the hollow connector 35, the door 30a of the cell manipulation chamber 30, and the door 40a of the cell cultivation chamber 40 with no space therebetween. From the sterilization gas generator 10 of the sterilizer 1', the sterilization gas is supplied to the cell manipulation chamber 30 through the pipes 162 and 304, and the sterilization gas is supplied to the connector 35 through the pipes 163 and 351. The cell manipulation chamber 30 is provided with, for example, globes 3a, 3b, and 3c and a centrifuge 5.

The sterilization chamber 11' of the sterilizer 1' and one side (the left side in FIGS. 12A and 12B) of the cell manipulation chamber 30' of the isolator 3' are connected to each other through the second door 112' of the sterilization chamber 11' with no space therebetween. The other side (the right side in FIGS. 12A and 12B) of the cell manipulation chamber 30' of the isolator 3' and the cell cultivation chamber 40' of the incubator 4' are connected to each other through the hollow connector 35', the door 30a' of the cell manipulation chamber 30', and the door 40a' of the cell cultivation chamber 40' with no space therebetween. From the sterilization gas generator 10 of the sterilizer 1', sterilization gas is supplied to the cell manipulation chamber 30' through pipes 162' and 304', and the sterilization gas is supplied to the connector 35' through pipes 163' and 351'. The cell manipulation chamber 30' is provided with, for example, globes 3a', 3b', and 3c' and a centrifuge 5'.

With the isolator system 6' configured as above, for example, cells cultured by the two incubators 4 and 4' or articles necessary for cultivation can be sterilized by the single common sterilizer F.

<Isolator System 6">

The isolator system 6" shown in FIGS. 13A and 13B includes two isolators 3 and 3" and one sterilizer 1'. The sterilizer 1' is the same as that in FIGS. 12A and 12B.

The relationship between the sterilization chamber 11' of the sterilizer 1', the cell manipulation chamber 30 of the isolator 3, and the cell cultivation chamber 40 of the incubator 4 is the same as that in FIG. 12.

The relationship between the sterilization chamber 11' of the sterilizer 1', a cell manipulation chamber 30" of the isolator 3", and the cell cultivation chamber 40' of the incubator 4' is the same as that in FIG. 12, except for the shape of the cell manipulation chamber 30".

As shown in FIGS. 13A and 1313, from the sterilization gas generator 10 of the sterilizer 1', the sterilization gas is supplied to the Op chamber 24 through the pipes 184 and 164.

With the isolator system 6" configured as above, for example, cells cultured by the two incubators 4 and 4' or articles necessary for cultivation can be sterilized by the single common sterilizer 1', and in the Op chamber 24 which is not connected to the isolator system 6" through a door, the article or the chamber can be sterilized.

The above-described embodiment is provided for ease of understanding of the invention, and it is not to be construed as limiting the invention. It should be noted that changes or improvements of the invention may be made without departing from the scope of the invention. The equivalents still fall within the scope of the invention.

Although in the above-described embodiment, hydrogen peroxide gas is used as sterilization gas, the invention is not limited thereto. For example, ozone or the like may be used.

What is claimed is:

1. A sterilizer which is connectable to an external chamber, the sterilizer comprising:
   a sterilization gas generator configured to generate sterilization gas;
   a sterilization chamber; and
   a gas supply system comprising:
      a first gas supply system configured to supply the sterilization gas from the sterilization gas generator to the sterilization chamber;
      a second gas supply system configured to supply the sterilization gas from the sterilization gas generator to the external chamber; and
      a first circulation system configured to circulate the sterilization gas, air, or a mixture thereof in the sterilization chamber, wherein the first circulation system comprises an in-line circulator such that said sterilization gas, air or a mixture thereof circulates through the circulator and bypasses the sterilization gas generator;
   wherein the gas supply system includes a gas inlet port which is configured to collect the sterilization gas supplied to the external chamber therethrough and a filter provided downstream of the gas inlet port.

2. The sterilizer as set forth in claim 1, wherein the sterilization chamber includes a gas feeding port which is configured to supply the sterilization gas to the sterilization chamber therethrough, and
   wherein the first gas supply system includes the gas feeding port and the second gas supply system does not include the gas feeding port.

3. The sterilizer as set forth in claim 1, further comprising a gas outlet port which is configured to supply the sterilization gas to the external chamber therethrough,
   wherein the second gas supply system includes the gas outlet port and the first gas supply system does not include the gas outlet port.

4. The sterilizer as set forth in claim 1, wherein the sterilization chamber includes a first door which is configured to transfer a sterilization target article to or from the outside of the sterilizer therethrough and a second door which is configured to transfer the sterilization target article between the sterilization chamber and the external chamber therethrough.

5. The sterilizer as set forth in claim 1, further comprising a housing in which the sterilization gas generator, the sterilization chamber and the gas supply system are provided.

6. The sterilizer as set forth in claim 1, wherein the gas supply system includes a plurality of gas outlet ports which are configured to supply the sterilization gas to a plurality of external chambers therethrough.

7. A sterilizer which is connectable to an external chamber, the sterilizer comprising:
   a sterilization gas generator configured to generate sterilization gas;
   a sterilization chamber; and
   a gas supply system comprising:
      a first gas supply system configured to supply the sterilization gas from the sterilization gas generator to the sterilization chamber;

a second gas supply system configured to supply as from the sterilization gas generator to the external chamber; and a first circulation system configured to circulate the sterilization gas, air, or a mixture thereof in the sterilization chamber, wherein the first circulation system comprises an in-line circulator such that said sterilization gas, air or a mixture thereof circulates through the circulator and bypasses the sterilization gas generator;

wherein the sterilization chamber includes a gas discharging port which is configured to discharge the sterilization gas from the sterilization chamber therethrough, and wherein the first gas supply system includes the gas discharging port and a filter provided downstream of the gas discharging port.

8. A sterilizer which is connectable to an external chamber, the sterilizer comprising:

a sterilization gas generator configured to generate sterilization gas;

a sterilization chamber; and a gas supply system comprising:

a first gas supply system configured to supply the sterilization gas from the sterilization gas generator to the sterilization chamber;

a second gas supply system configured to supply the sterilization gas from the sterilization gas generator to the external chamber; and a first circulation system configured to circulate the sterilization gas, air, or a mixture thereof in the sterilization chamber, wherein the first circulation system comprises an in-line circulator such that said sterilization gas, air or a mixture thereof circulates through the circulator and bypasses the sterilization gas generator;

wherein the gas supply system further comprises a first substitution system configured to substitute the sterilization gas in the sterilization chamber with air passing through a filter and a second substitution system configured to substitute the sterilization gas in the external chamber with air passing through a filter, and wherein the first and second substitution systems each include an atmosphere-side opening end and a sterilization gas reduction catalyst provided in the atmosphere-side opening end.

9. The sterilizer as set forth in claim 8, wherein the sterilization gas is hydrogen peroxide gas made from hydrogen peroxide solution, and wherein the catalyst has a function to detoxify the hydrogen peroxide gas.

10. An isolator system comprising: the sterilizer as set forth in claim 1; and an external chamber connected to the sterilizer.

11. The isolator system as set forth in claim 10, wherein the external chamber is a cell manipulation chamber of an isolator.

12. The sterilizer as set forth in claim 1, wherein the first circulation system circulates the sterilization gas supplied by the first gas supply system.

13. The sterilizer as set forth in claim 1, further comprising a controller, wherein the controller switches operation between the first gas supply system and the first circulation system.

14. A sterilizer which is connectable to an external chamber, the sterilizer comprising:

a sterilization gas generator configured to generate sterilization gas;

a sterilization chamber; and a gas supply system comprising:

a first gas supply system configured to supply the sterilization gas from the sterilization gas generator to the sterilization chamber;

a second gas supply system configured to supply the sterilization gas from the sterilization gas generator to the external chamber; and a first circulation system configured to circulate the sterilization gas, air, or a mixture thereof in the sterilization chamber, wherein the first circulation system comprises an in-line circulator such that said sterilization gas, air or a mixture thereof circulates through the circulator and bypasses the sterilization gas generator;

wherein the first gas supply system is configured to supply the sterilization gas to the sterilization chamber without the sterilization gas passing through a filter prior to entering the sterilization chamber and to discharge the sterilization gas from the sterilization chamber through a filter.

15. The sterilizer as set forth in claim 14, wherein the filter through which the sterilization gas is discharged from the sterilization chamber is in contact with the sterilization chamber.

16. The sterilizer as set forth in claim 1, wherein the gas supply system further comprises a first substitution system configured to substitute the sterilization gas in the sterilization chamber with air passing through a filter, wherein said filter is optionally sterilized by operations of the first gas supply system and the first circulation system.

17. The sterilizer as set forth in claim 16, wherein the filter is in contact with the sterilization chamber.

18. The sterilizer as set forth in claim 1, wherein the first gas supply system supplies the sterilization gas to the sterilization chamber without the sterilization gas passing through a filter prior to entering the sterilization chamber, and the second gas supply system supplies the sterilization gas to the external chamber without the sterilization gas passing through a filter prior to entering the external chamber.

* * * * *